United States Patent [19]

Cunningham

[11] 4,065,964
[45] Jan. 3, 1978

[54] PORTABLE MACHINE FOR TESTING PROTECTIVE COATINGS

[75] Inventor: Richard D. Cunningham, Omaha, Nebr.

[73] Assignee: Northern Natural Gas Company, Omaha, Nebr.

[21] Appl. No.: 754,027

[22] Filed: Jan. 24, 1977

[51] Int. Cl.² ............................................... G01N 3/56
[52] U.S. Cl. ................................................... 73/150 A
[58] Field of Search ...................... 73/150 R, 150 A, 7; 118/9, 35, 56

[56] References Cited

U.S. PATENT DOCUMENTS

| 2,718,779 | 9/1955 | McLean | 73/7 |
| 3,208,271 | 9/1965 | Thompson | 73/150 R X |
| 3,985,026 | 10/1976 | Griffin et al. | 73/150 R |

OTHER PUBLICATIONS

*Peel Resistance Accurately Measured*, in Materials Research & Standards, p. 435, Aug. 1965.

*Primary Examiner*—Richard C. Queisser
*Assistant Examiner*—Joseph W. Roskos
*Attorney, Agent, or Firm*—Zarley, McKee, Thomte, Voorhees & Sease

[57] ABSTRACT

A portable machine for testing protective coatings which have been applied to pipes or the like comprising a portable frame adapted to be hand-held by testing personnel. A pair of elongated arms extend from the portable frame and have pipe shoes on one end thereof adapted to embrace the pipe so that the portable frame will be maintained at a predetermined distance from the pipe during the testing operation. A cutting blade is provided for severing the protective coating from the pipe and has an elongated flexible member connected thereto. A power assembly is secured to the frame and is operatively connected to the elongated flexible member to cause the elongated flexible member and the cutting blade to be moved towards the support to sever the protective coating from the pipe. A force read-out device is connected to the power assembly for indicating the amount of force required to sever the protective coating from the pipe.

10 Claims, 5 Drawing Figures

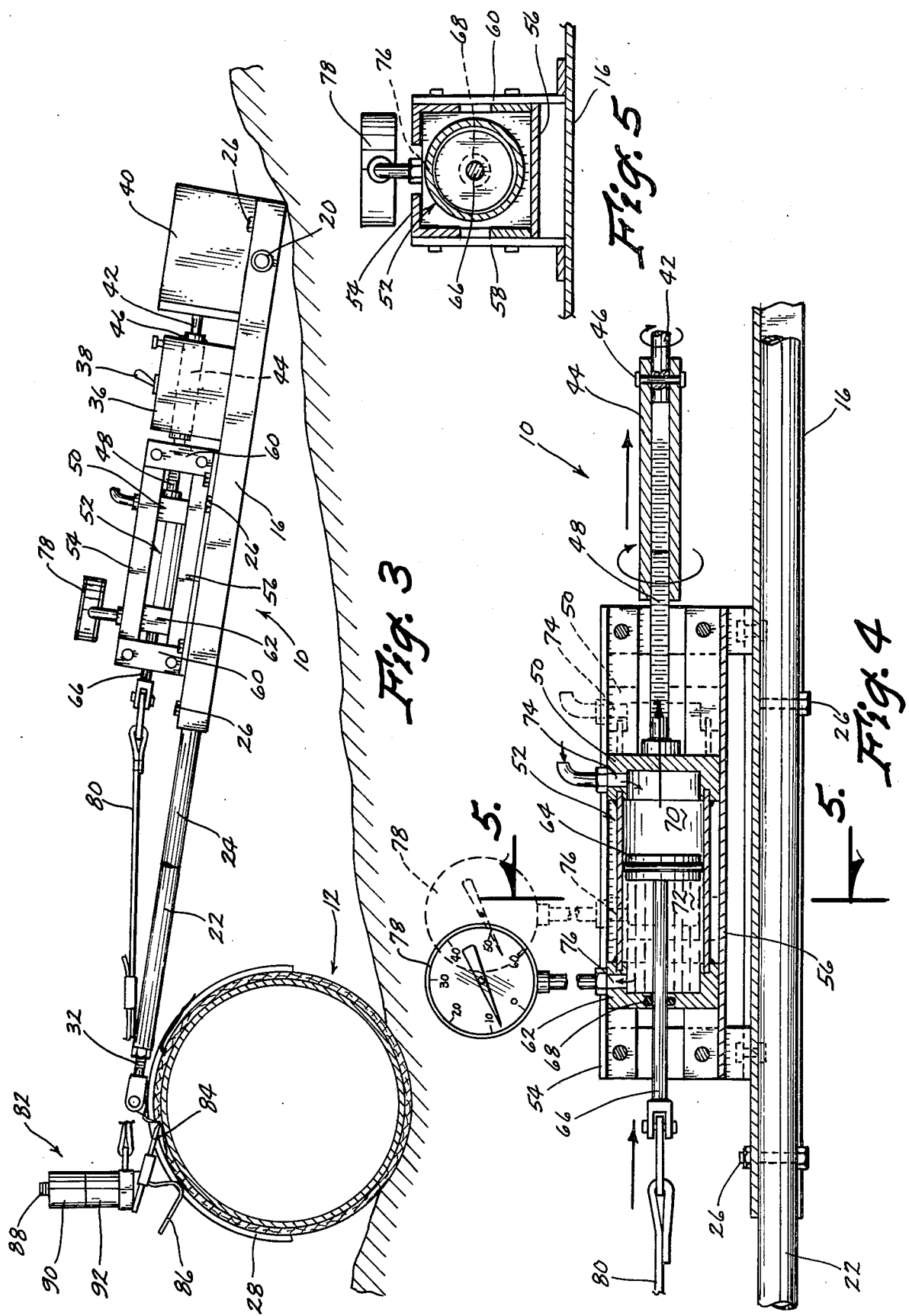

PORTABLE MACHINE FOR TESTING PROTECTIVE COATINGS

BACKGROUND OF THE INVENTION

This invention relates to a small portable machine for testing adhesion coatings to various substrates such as pipes or the like.

Good adhesion is essential for good performance of a coating in most industrial applications, with one exception being strippable coatings. A good coating system involves:

1. Selecting a coating with properties permitting it to adhere to the substrate's surface.
2. Preparing the substrate surface properly.
3. Applying the coating so it will achieve good adhesion.

If adhesion performance of a coating material is not known, some means must be available to determine the degree of adhesion and to relate it to some base value. Unfortunately, there are no commonly accepted absolute criteria of adhesion values expressible in concrete terms. Many adhesion tests involve subjective judgments. Even numbers obtained from machine performed tests are not clearly defined.

There are many laboratory type machines presently available for testing adhesion of a protective coating on a specially-prepared panel. The panels are ordinarily prepared in a laboratory under ideal conditions.

U.S. Pat. No. 2,533,076 issued to D. M. Williams on Dec. 5, 1950 and is directed to an apparatus for testing the adhesion of films of coating material. The Williams apparatus is not of the portable type and is designed to test the adhesion characteristics of flat surface films. U.S. Pat. No. 2,530,257 issued to J. R. Marcus on Nov. 14, 1950 and discloses an apparatus for testing coatings applied to a flat surface. More particularly, the Marcus device is designed to test the mar resistance and scratch adhesion of paints and is not portable. U.S. Pat. No. 3,124,955 issued to G. E. Naslund on Mar. 17, 1964 and involves a pendulum type apparatus designed to determine the adherence of a coating bonded to a surface. In Naslund, an elongated strip of tape must be adhered to the flat test surface so that the swinging pendulum will strike the tape and the amount of force required to separate the tape from the surface is recorded by an indicator arm. U.S. Pat. No. 2,498,265 issued to H. Green on Feb. 21, 1970 and relates to a non-portable apparatus for testing the adherence of coating films on a flat surface.

Coatings, especially pipe-line coatings, applied in the field are not applied under ideal conditions; and, therefore, do not always perform as expected. Adhesion may deteriorate with time due to temperature variations, soil stresses, ground water and natural aging of the coating. Currently, the available testing machines cannot be used for testing in-place coatings. A common procedure for testing in-place coatings in the pipe-line industry is to scribe an "x" through the coating into the substrate with a sharp knife. Then, holding the knife at a 35° to 40° angle, the blade point is inserted at an intersection of the scribe and pushed into the coating firmly and constantly while making mental notes of the force required, flaking caused, and degree of adhesion of the coating. The degree of adhesion is then rated against a similar test performed on an unexposed or control panel.

Therefore, it is a principal object of the invention to provide a small portable machine for testing adhesion of coatings to various substrates.

A further object of the invention is to provide a small portable machine which may be used for testing adhesions of coatings while the coating is in place.

A still further object of the invention is to provide a machine for testing adhesion of coatings which allows evaluation of the coating system after the coating system has been applied in the field under conditions which may be far from ideal.

A still further object of the invention is to provide a machine for testing adhesion of coatings which does not require special operator training.

A still further object of the invention is to provide a machine for testing adhesion of coatings including means for visually indicating the force required to sever the coating from the substrate.

A still further object of the invention is to provide a machine for testing adhesion of coatings including means for varying the amount of weight applied to the knife blade associated therewith.

A still further object of the invention is to provide a machine for testing adhesion of coatings to various substrates which is economical to manufacture, durable in use and refined in appearance.

These and other objects will be apparent to those skilled in the art.

BRIEF DESCRIPTION OF THE DRAWINGS

FIG. 3 is a sectional view as seen on lines 3—3 of FIG. 2:

FIG. 4 is an enlarged sectional view as seen on lines 4—4 of FIG. 2; and

FIG. 5 is a sectional view seen on lines 5—5 of FIG. 4.

SUMMARY OF THE INVENTION

Figure 1:
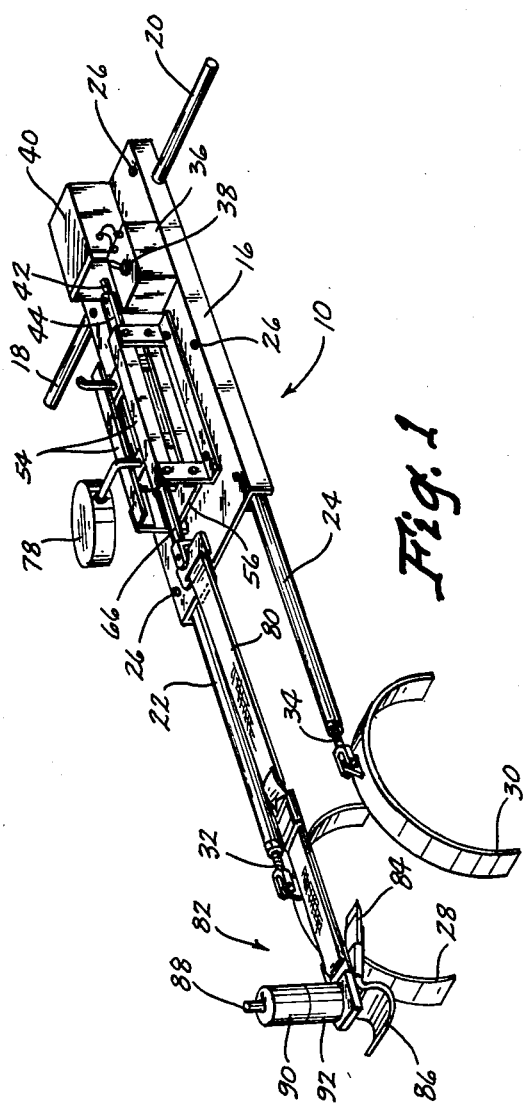
FIG. 1 is a perspective view of the machine of this invention.

The invention comprises a small portable machine which may be used to test the adhesion of protective coatings on substrates such as pipes or the like. The invention comprises a small portable frame means having handles extending outwardly from one end thereof and pipe positioning means extending from the other end thereof which are employed to maintain the device in a predetermined spaced position relative to the pipe. A battery-driven screw-jack motor is mounted on the support and is operatively connected to one end of a power cylinder. The power cylinder is provided with a piston mounted therein having a cylinder rod extending outwardly from one end thereof. The location of the piston within the cylinder defines first and second compartment areas. The first compartment area is in communication with the atmosphere. The second compartment area is preferably filled with oil and is in communication with a pressure gauge. An elongated flexible strap is connected at one of its ends to the cylinder rod and has a knife blade apparatus at its other end for severing the protective coating from the pipe. The knife blade is placed in engagement with the protective coating and the screw jack motor is energized to pull the knife blade towards the support to sever the protective coating from the pipe. The amount of force required to sever the protective coating from the pipe is indicated by the pressure gauge.

DESCRIPTION OF THE PREFERRED EMBODIMENT

The machine of this invention is referred to generally by the reference numeral 10 while the reference numeral 12 will refer to a pipe having a protective coating 14 applied to the outer surface thereof.

Machine 10 generally comprises a support or frame means 16 having a pair of handles 18 and 20 extending laterally therefrom adjacent one end thereof. A pair of positioning arms 22 and 24 are secured to the support 16 by bolts 26 and extend from the support 16 as indicated in the drawings. Pipe shoes or clamps 28 and 30 are pivotally connected to the ends of bolts 32 and 34 which are selectively adjustably mounted in the outer ends of the positioning arms 22 and 24.

The numeral 36 indicates a power source such as a D.C. battery mounted on the support 16 and controlled by means of switch 38. Power source 36 is operatively electrically connected to a reversible screw-jack motor 40 having a rotatable power shaft 42 extending therefrom which has an internally threaded coupler 44 secured thereto by pin 46. One end of threaded shaft 48 is threadably received by the coupler 44 as illustrated in FIG. 4. The other end of shaft 48 is rigidly secured by welding or the like to end 50 of cylinder 52. Cylinder 52 is longitudinally slidably mounted between a pair of channels 54 and 56 which are secured to the support 16 by support members 58 and 60. Ends 50 and 62 of cylinder 52 have the same cross-sectional configuration as defined by the channels 54 and 56 so that the cylinder 52 will not rotate upon the coupler 44 being rotated as will be described in more detail hereinafter.

Cylinder 52 is provided with a piston 64 mounted therein which has a cylinder rod 66 secured thereto and extending outwardly through end 62. As seen in FIG. 5, seal 68 embraces rod 66 at the location where rod 66 passes outwardly through end 62. Piston 64 defines compartment areas 70 and 72 at opposite sides thereof within cylinder 52. Compartment area 70 communicates with the atmosphere by means of the port 74. Preferably, compartment area 72 is filled with hydraulic fluid or the like. Cylinder 52 is provided with a port 76 which communicates with the compartment area 72 and which has a pressure gauge 78 opertively placed in communication therewith so that the pressure within compartment area 72 will be registered on the pressure gauge 78.

Figure 2:
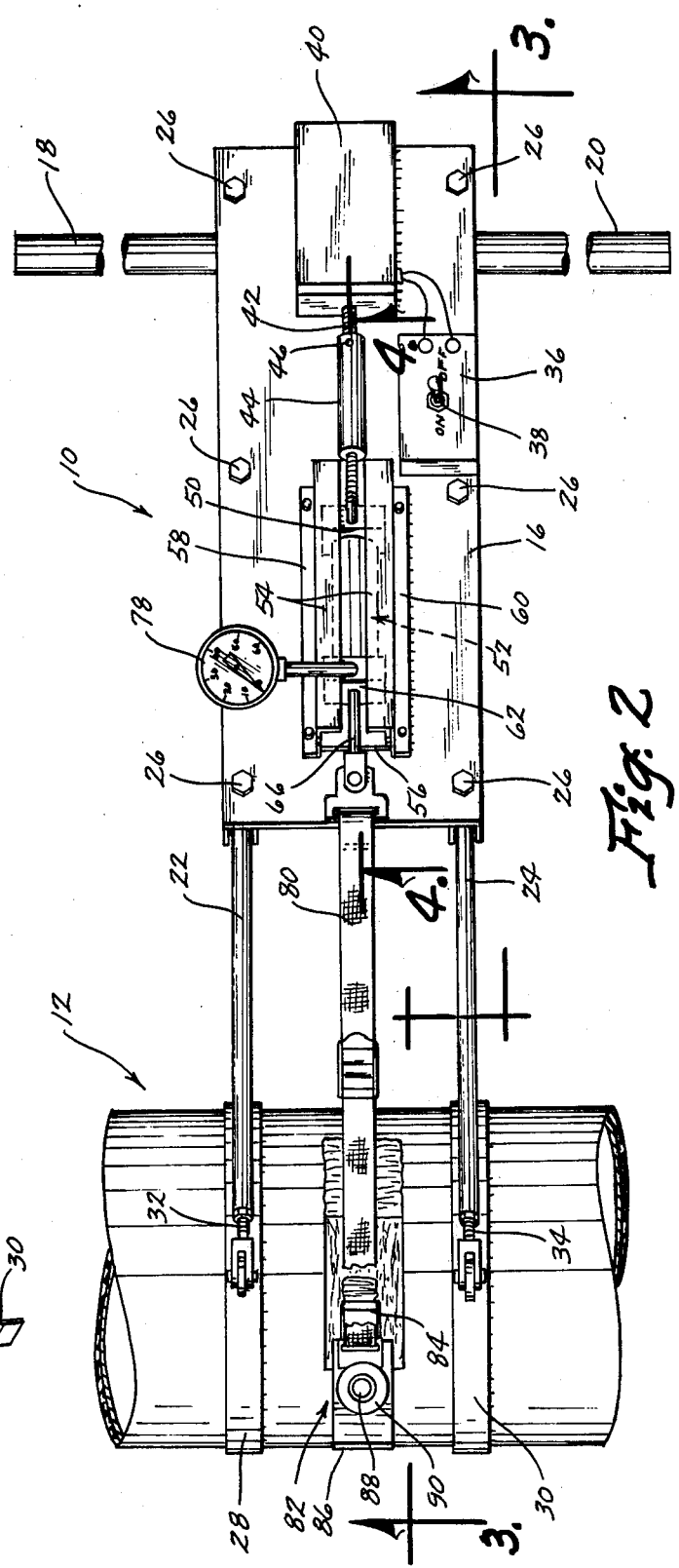
FIG. 2 is a top elevational view of the device.

The elongated flexible strap 80 is operatively secured at one end thereof to the rod 66 as seen in FIGS. 2 and 4. The other end of strap 80 is secured to a cutting knife or blade assembly referred to generally by the reference numeral 82. Assembly 82 includes a knife blade 84 which extends downwardly and outwardly as illustrated in the drawings. A blade guide 86 extends from the blade 84 as illustrated in FIG. 3 and is adapted to engage the pipe in the manner illustrated in FIG. 3 so that the proper blade angle is maintained during the testing operation. Assembly 82 also includes an upstanding post 88 upon which may be placed weights 90 and 92 to permit the amount of weight applied to the assembly to be varied as required in different testing operations.

An example for using the apparatus to test adhesion of pipe-line coatings will be used to describe the operation of the machine. The apparatus, however, is not limited to testing pipe-line coatings since simple modifications will allow it to be used on any type of coated substrate. The first step in using the machine is to apply a 5 to 6 inch length of masking tape to the coating tangential to the pipe 12. The width of the tape should be the same as the knife blade 84. A sharp knife is then used to cut through the coating to the substrate along the boundary of the tape. The shoes 28 and 30 are then mounted on the pipe 12 as illustrated in FIG. 2 so that the blade 84 will be aligned with the previously determined area to be tested. The knife blade 84 is then placed in engagement with the coating and is maintained at the proper angle with respect thereto by means of the guide 86.

The support 16 may either be hand held by the operator by means of the handles 18 and 20 or simply may be placed in ground engagement as illustrated in FIG. 3. The constant speed screw-jack motor 40 is then energized so that the power shaft 42 is rotated as indicated by the arrow in FIG. 4. Rotation of shaft 42 causes coupler 44 to be rotated so that threaded shaft 48 will be threadably drawn inwardly into the coupler 44 as illustrated by the straight arrow in FIG. 4. As shaft 48 is moved inwardly into coupler 44, cylinder 52 is moved to the right as viewed in FIG. 4. Movement of the cylinder 52 towards motor 40 causes the knife blade 84 to be moved towards the machine so that the coating 14 is severed from the pipe 12. If the blade 84 experiences no resistance in separating the coating from the pipe, pressure gauge 78 will not indicate any rise in pressure within compartment area 72. If resistance is experienced by the blade 84, the resistance or force required to sever the coating from the pipe is transmitted to the piston 64 which then tends to compress the fluid within the compartment area 72 and the increased pressure within compartment 72 is indicated on the pressure gauge 78. Thus, the more force required to remove or sever the coating from the surface will be indicated with higher readings on the pressure gauge 78 and vice versa.

It is suggested that approximately five or six separate tests be conducted on the pipe at each location so that an average may be taken of the readings.

It should be noted that the screw jack motor is of the constant speed type to enable a comparison between successive tests. It should also be noted that the motor could be driven from an automobile battery or the like.

Thus it can be seen that a novel portable machine has been provided for testing in-place coatings which achieves all of its stated objectives.

I claim:
1. A portable machine for testing protective coatings, comprising,
a portable support means,
positioning means connected to said support means for positioning said support means relative to the object having the protective coating thereon,
a blade means for severing the protective coating from said object,
an elongated member connected at one end to said blade means,
power means on said support means operatively connected to the other end of said elongated member for moving said elongated member and said blade means towards said support means to sever the protective coating from said object,
and force readout means operatively connected to said power means for indicating the amount of force required to sever the protective coating from the object.

2. The machine of claim 1 wherein said positioning means comprises a pair of spaced apart arms secured to and extending from said support means, and a clamp means secured to said arms.

3. The machine of claim 2 wherein said clamp means comprises a pipe shoe adapted to partially embrace a pipe.

4. The machine of claim 1 wherein said power means comprises a screw jack motor, said force readout means comprising a hydraulic cylinder having a piston positioned therein to define first and second compartment areas on opposite sides of said piston, said first compartment area having fluid therein, a cylinder rod secured to said piston and extending through said first compartment area and outwardly from said cylinder, said cylinder rod being selectively secured to said elongated member, said cylinder being operatively secured to said screw jack motor whereby actuation of said screw jack motor will cause said cylinder, cylinder rod, elongated member and said blade means to be moved relative to said support means, and a pressure gauge in communication with said first compartment area for indicating the pressure created in said first compartment area as said blade means is severing the protective coating from the object.

5. The machine of claim 4 wherein said second compartment area is in communication with the atmosphere.

6. The machine of claim 1 wherein said blade means has a guide means mounted thereon for maintaining said blade means in the proper attitude relative to the object having the protective coating thereon.

7. The machine of claim 1 wherein an adjustable weight means is provided on said means for maintaining said blade means in severing engagement with the protective coating.

8. The machine of claim 1 wherein said power means comprises a battery operated screw jack motor.

9. The machine of claim 1 wherein said elongated member is flexible.

10. The machine of claim 1 wherein a handle means is secured to said support means.

* * * * *